United States Patent [19]

Beaudoin et al.

[11] Patent Number: 4,925,520
[45] Date of Patent: May 15, 1990

[54] APPARATUS FOR APPLYING AN ELASTIC WAISTBAND TRANSVERSELY OF A LONGITUDINALLY MOVING WEB

[75] Inventors: Henry J. Beaudoin, Sheboygan Falls; Donald W. Lammers, Oostburg; John A. McCabe, Sheboygan Falls, all of Wis.

[73] Assignee: Curt G. Joa, Inc., Boynton Beach, Fla.

[21] Appl. No.: 230,893

[22] Filed: Aug. 11, 1988

[51] Int. Cl.$^5$ .............................................. B32B 31/06
[52] U.S. Cl. ....................... 156/494; 26/90; 156/164; 156/229; 156/519; 156/521; 156/552; 156/567
[58] Field of Search ............... 156/160, 161, 163, 164, 156/229, 434, 439, 494, 495, 496, 519, 552, 568, 567, 521; 26/88, 90; 28/102

[56] References Cited

U.S. PATENT DOCUMENTS

| | | | |
|---|---|---|---|
| 30,801 | 12/1860 | Cleveland | 26/90 |
| 1,014,916 | 1/1912 | Stevens | 156/439 |
| 2,543,220 | 2/1951 | Ardell | 156/521 |
| 2,692,635 | 10/1954 | Polley | 156/439 |
| 2,702,406 | 2/1955 | Reed | 26/88 X |
| 3,565,724 | 2/1971 | Yamaguchi | 156/521 |
| 3,570,137 | 3/1971 | Fleissner | 26/90 X |
| 3,805,341 | 4/1974 | Jense | 156/439 X |
| 3,957,570 | 5/1976 | Helm | 156/519 |
| 4,293,367 | 3/1981 | Klasek et al. | 156/494 |
| 4,523,969 | 12/1985 | Spencer | 156/161 |
| 4,525,229 | 6/1985 | Suzuki et al. | 156/229 X |
| 4,735,673 | 2/1988 | Piron | 156/496 |

Primary Examiner—David Simmons
Attorney, Agent, or Firm—Fuller, Puerner & Hohenfeldt

[57] ABSTRACT

An elastic ribbon is fed over a vacuum drum. Rotating cutter blades use the drum as an anvil to cut the ribbon into spaced apart segments. A sheet comprising a diaper web runs over a roll that is spaced from the drum. A segment transferring and stretching device is arranged between the drum and roll. One embodiment of the transferring device has grippers rotating together about the axes that are not coaxial but are at opposite acute angles relative to the roll and drum axes. The grippers engage an unstretched elastic segment on the drum when the grippers are close together but as they rotate they spread apart and stretch the segment which is then pressed onto the glue treated sheet. In another embodiment of the elastic segment stretching and transferring device, grippers are mounted to the periphery of a vacuum drum. At least one of the grippers is moved alternately toward and away from the other under the influence of a stationary cam as the drum rotates.

2 Claims, 7 Drawing Sheets

APPARATUS FOR APPLYING AN ELASTIC WAISTBAND TRANSVERSELY OF A LONGITUDINALLY MOVING WEB

BACKGROUND OF THE INVENTION

This invention pertains to apparatus for installing waistbands in a web comprising apparel that is worn on the body such as disposable diapers.

The presently most popular type of disposable diaper comprises a thin flexible liquid impermeable backing sheet on which a permeable nonwoven sheet is overlayed. An absorbent pad is disposed between the two sheets and the sheets are adhered at their edges to form a unitary article and provide for preventing liquid body exudates from seeping out of the edges of the diaper. Most diapers on the market also have longitudinally extending elastic bands adhered to the sheets on each side of the absorbent pad. These bands cause the diaper to engage the legs of the wearer snuggly so as to prevent leakage along the interface of the nonwoven sheet which is in contact with the body.

It is regarded as desirable to have elasticity in the waist regions of the diaper to create a gentle pressure for inhibiting the diaper from slipping down and for preventing the leakage such as might occur when the wearer is lying down. Various methods and apparatus have been devised for inserting an elastic member in the waistband region. Doing this is problematical because the diapers are formed as a web which is moving longitudinally at a high rate. Any elastic segment that is to be inserted in the waistband area of an individual diaper will extend transversely to the longitudinally moving web and must be deposited in a stretched condition on the web while it is in motion. The invention disclosed herein constitutes a new method and apparatus for inserting transversely extending elastic segments in the waist area of diapers and similar body wearable garments.

SUMMARY OF THE INVENTION

In general terms, the new apparatus comprises a rotatable vacuum drum. A ribbon of elastic material is fed onto the drum in its direction of rotation and held on the drum by means of vacuum. A knife roll has blades which rotate contiguous to the vacuum roll for cutting off segments of the ribbon with regular periodicity. The segments are carried rotationally on the drum. A transfer roll is rotating in parallelism with the vacuum drum and there is a space between the peripheries of the vacuum drum and transfer roll. A pair of radially extending gripper members are driven rotationally between the drum and transfer roll. When the grippers are aligned with and contiguous to the periphery of the vacuum drum, the grippers are close to each other at which time they can grip the unstretched segment that is in the proper rotational relationship with the grippers. Then, the grippers begin to separate laterally or transversely as they rotate and during further rotation they stretch the elastic segment that they have picked off the vacuum drum. Either the nonwoven facing sheet of the diaper web or the fluid impermeable backing sheet of the web or the complete web runs over a backup member in the form of a transfer roller or a fixed non-rotating platen. The sheet fed over the transfer roll is usually treated with adhesive before it arrives at this roll. Hence, when the grippers become contiguous to the sheet by itself, or when it is joined to the webs and the underlying transfer roll, the grippers are spread apart and the elastic segment is stretched and is pressed onto the moving sheet or web to be held on the sheet in a stretched condition by the adhesive.

The grippers have vacuum ports in the surfaces which press against the unstretched elastic segment for holding the segment as it is rotated and is stretched. An important feature of the grippers, however, which overcame the problem of vacuum force being insufficient to eliminate slipping as tension resulting from stretching continued to increase, is the provision of a plurality of pointed elements in the vicinity of the vacuum ports of the grippers which positively hold the segments until they are released for being maintained in a stretched condition by adhering to the sheet.

The foregoing features of the apparatus and other features will now be discussed in greater detail in reference to the drawings.

DESCRIPTION OF A PREFERRED EMBODIMENT

Figures 1, 2:
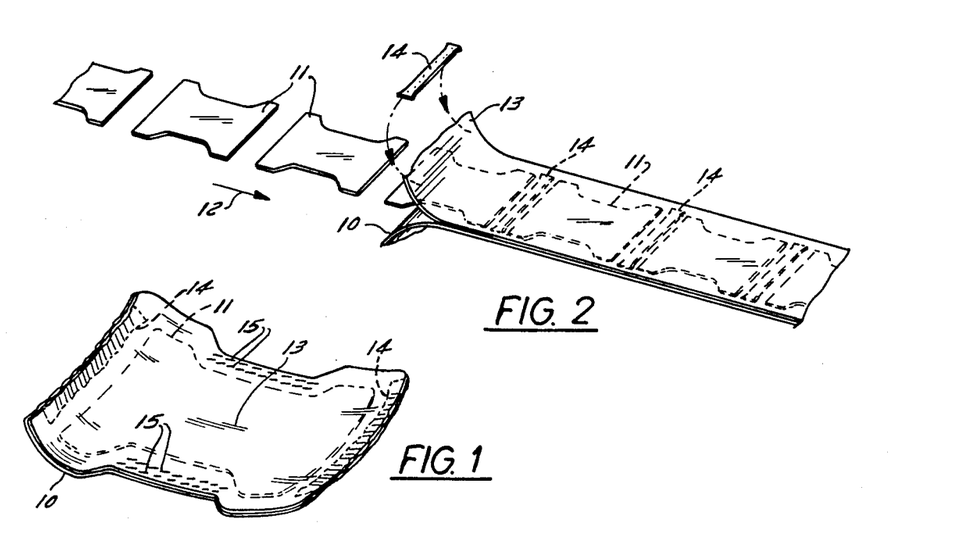
FIG. 1 depicts a typical disposable diaper in which elastic waistbands have been installed by the method and apparatus constituting the invention.
FIG. 2 is a diagram showing the components of a diaper and their relationship as diapers are being formed in a continuous web.

Attention is invited to FIGS. 1 and 2 for a brief description of a finished diaper and forming the web of diapers, respectively. Consider the longitudinally moving diaper web in FIG. 2 first. The web comprises a backing sheet 10 made of a fluid impermeable substance such as polyethylene. Prior to the backing sheet 10 reaching the position which it has attained in FIG. 2, continuous longitudinal stripes of glue, not shown, have been applied in parallelism with each other. The absorbent pads 11 are transported in the direction of the arrow 12 and are deposited on the adhesive containing surface of backing sheet 10. The backing sheet and absorbent pad are overlayed with a facing sheet 13 of a fluid permeable nonwoven material. Before the backing sheet 10 and facing sheet 13 are brought into interfacing relationship, a segment 14 of elastic material in a stretched condition is deposited on the side of facing sheet 13 which interfaces with the backing sheet 10 and absorbent pad 11. After the web is formed and the adhesives are set, somewhere along the production line the web is cut into individual diapers. The cut is made through the waistband region on the transversely extending centerline of a stretched elastic segment 14 so that half of the segment remains fixed in the waistband region of one diaper and the other half remains in the waistband region of the ensuing diaper.

FIG. 1 shows a completed diaper. The elastic waistbands 14 are fixed between nonwoven sheet 13 and impermeable backing sheet 10 at opposite ends of the diaper in this particular diaper style. The absorbent pad 11, which has an hourglass configuration, is also deposited between the two sheets and secured by the glue lines on each of the sheets. There are also elastic strings or bands, 15 extending along the margin of the absorbent pad 11, as is well known for keeping the diaper snuggly against the legs of the wearer. The elastic bands 15 were not mentioned in connection with discussing FIG. 2 but it will be understood that they are adhered, in stretched condition, to the side margins of either backing sheet 10 or facing sheet 13 before the two sheets are brought together. There are a variety of methods for inserting elastic bands 15 which are familiar to those involved in diaper making so it is unnecessary to discuss them.

Figure 3:
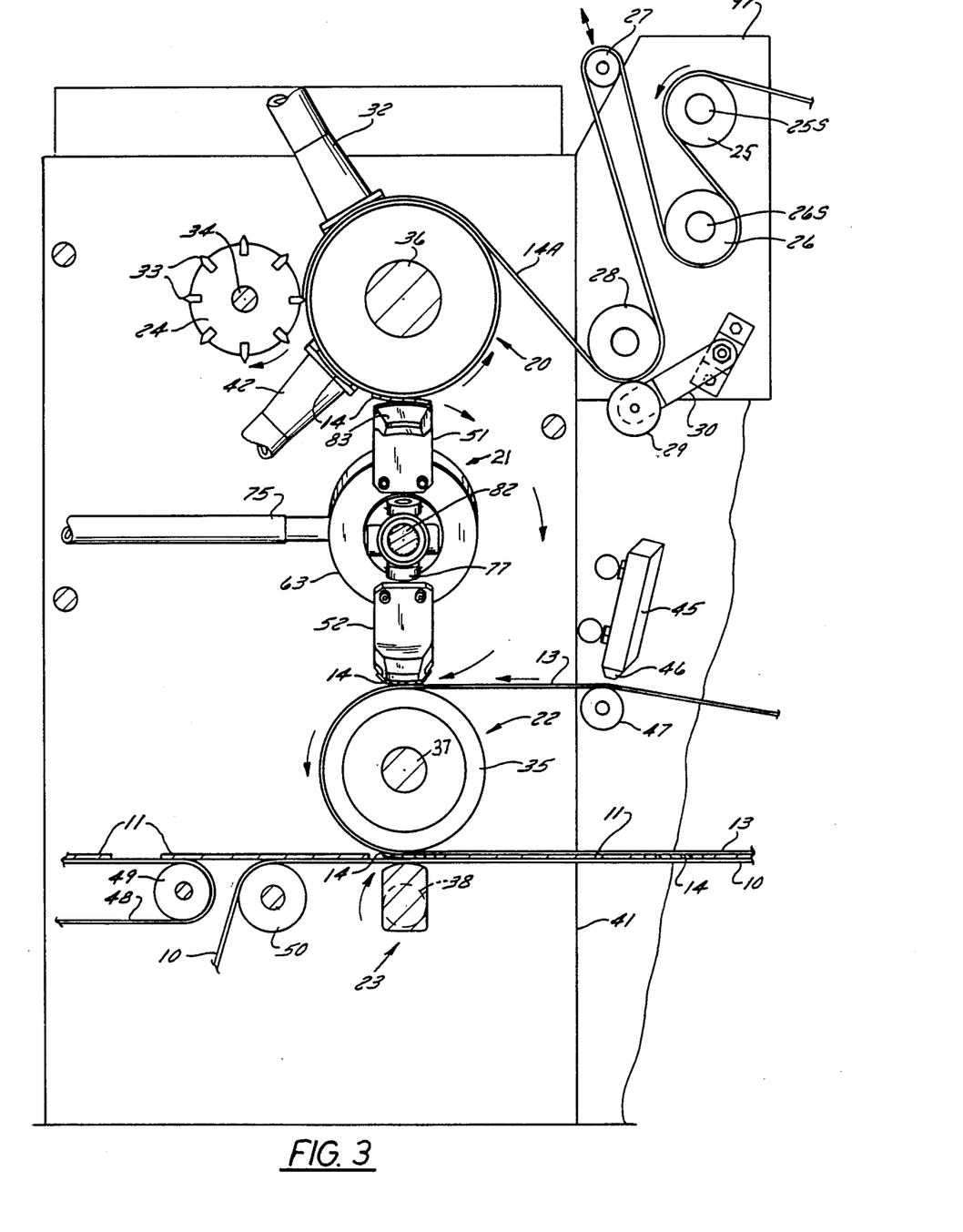
FIG. 3 shows the principal parts of the new elastic segment applying apparatus and shows how the sheets and absorbent pads are brought together to form a continuously moving web.

FIG. 3 shows the general arrangement of the parts of the apparatus for applying elastic waistbands transversely of a moving web. The principal components of the elastic waistband applicator are a vacuum roll or drum 20, an elastic segment transfer device 21, a backup member in the form of an elastomer coated transfer roll 22, a segment pressing element 23 and a knife roll 24 near the top of the drawing. A ribbon of elastic material 14A is fed onto the periphery of vacuum drum 20. This ribbon may be comprised of an elastic polyurethane foam material or it can be some other form of flexible elastic sheet. The ribbon is fed in a serpentine path over rolls 25 and 26 which are connected by gears, not visible in a gear box 97 (FIG. 4) and are driven by an adjustable speed dc motor, not shown. A known type of dancer roll 27 senses web tension and is involved in controlling the speed of rolls 25 and 26 so that relatively constant web tension is maintained between rolls 26 and 28. Knife roll 24 is driven from the vacuum drum 20 through gears, not visible. Roll 28 is driven by a timing belt, not visible in FIG. 3, from knife roll 24 and meters in the appropriate length of elastic ribbon 14A which determines the length of elastic segment 14. Elastic ribbon 14A is fed out or unrolled from a coil or reel, not shown. A roll 29 on a spring biased arm 30 pinches the ribbon 14A against roll 28.

Figures 5, 6, 7:
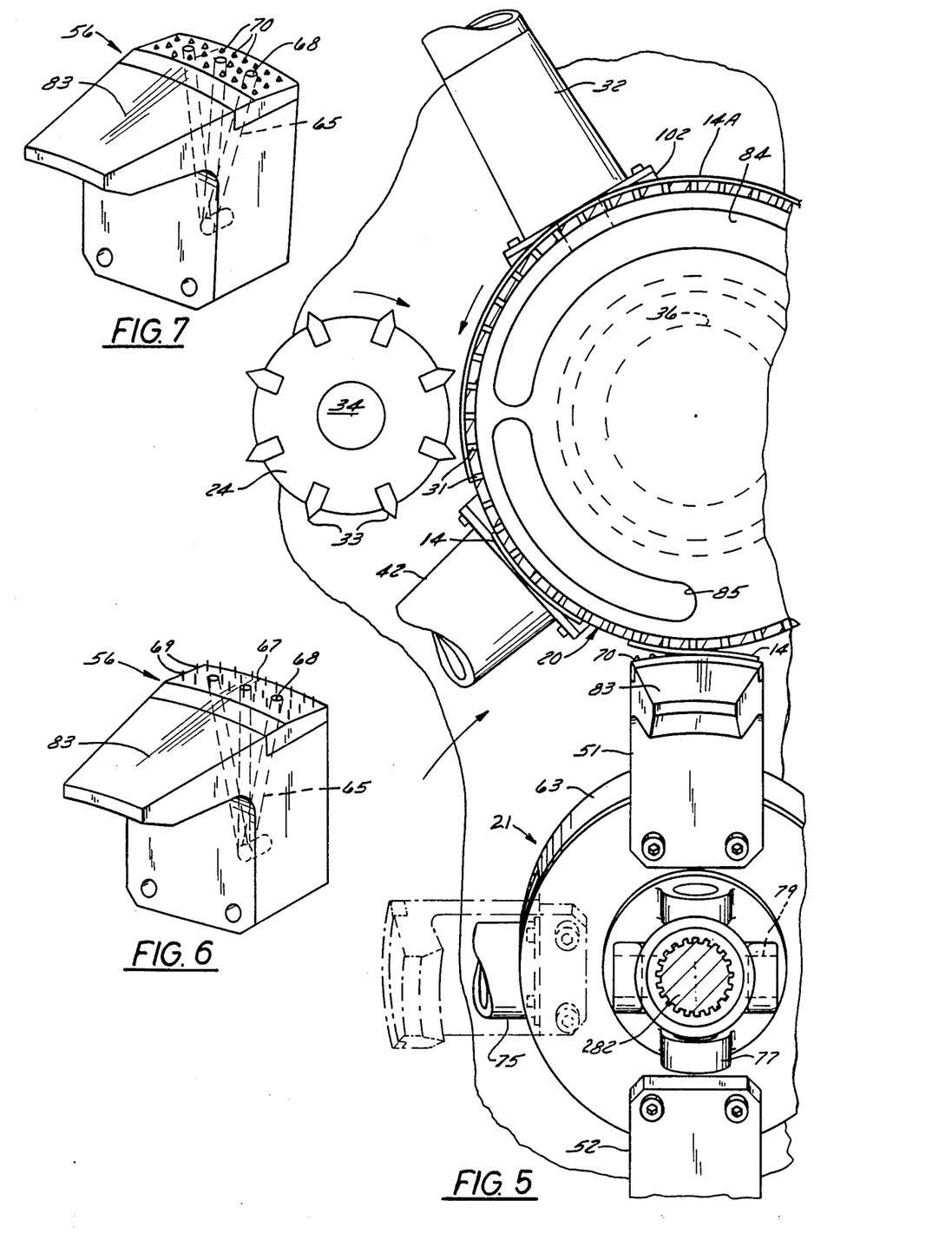
FIG. 5 is a side elevational view, with some parts in section, showing in greater detail the relationship of the vacuum drum, the knife roll and the elastic segment transferring and stretching means.
FIGS. 6 and 7 are perspective views of two different types of elastic segment grippers which are used in the waistband applying apparatus.

FIG. 5 shows a cross section of the vacuum drum 20 where one may see that it is provided in its periphery and over almost its entire axial length with a plurality of holes 31 through which vacuum is drawn. The vacuum holds the elastic segments 14 to the periphery of the vacuum drum 20 so the segments can be transferred from the point on the drum where they are cut from the ribbon to the new transfer means 21 by which they are taken off of the drum and applied to the sheet 13 of the diaper web as illustrated in FIG. 3.

Figure 4:
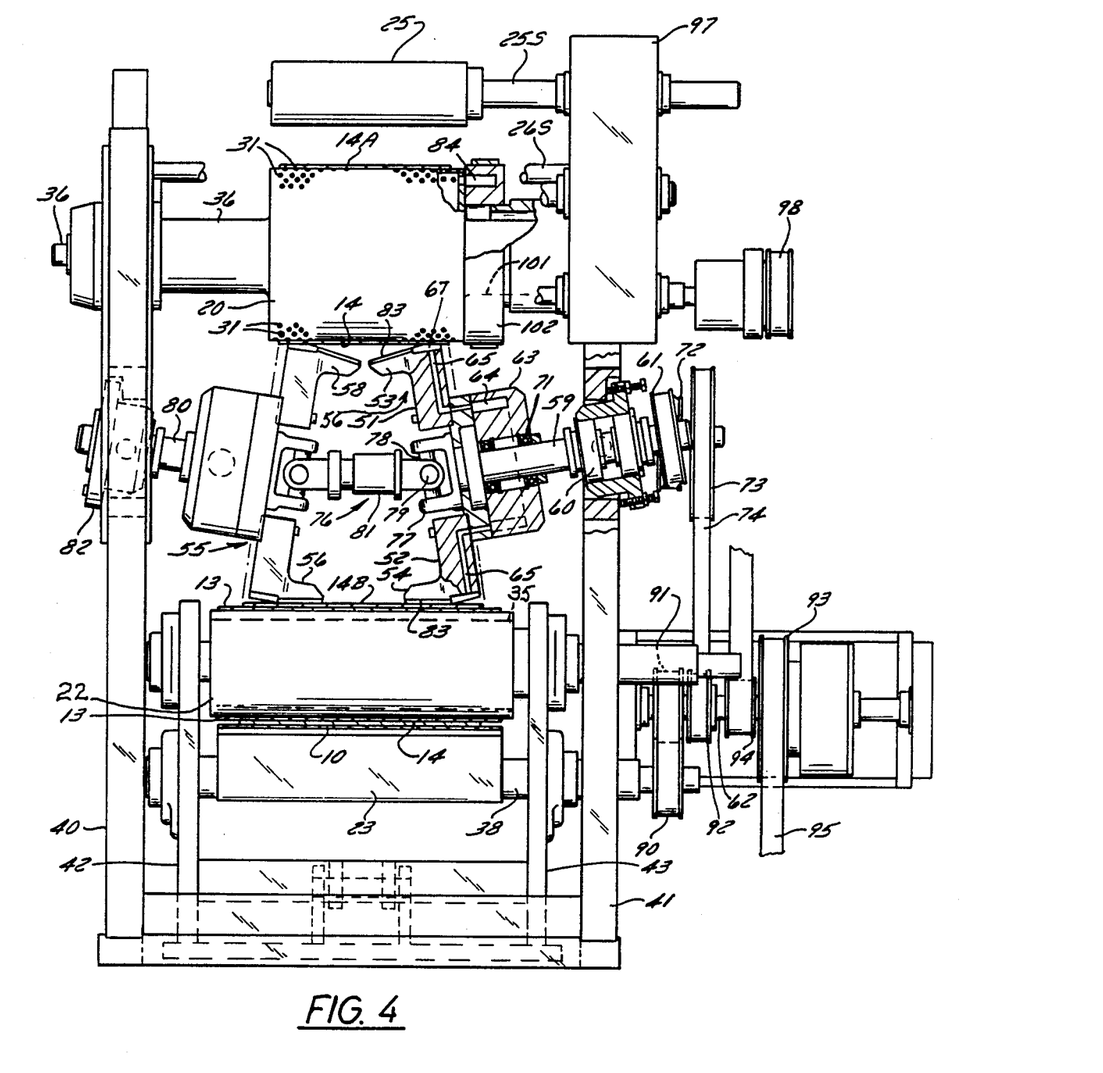
FIG. 4 is a front elevational view of the new apparatus for applying an elastic waistband transversely of a web that is moving longitudinally at a high rate of speed.

FIGS. 3 and 5 show vacuum pipes 32 and 42 which draw the vacuum inside of the drum 20. As can be seen especially well in FIG. 5, pipe 32 draws a low vacuum in the vacuum chamber 84 since before segment 14 is cut from the elastic ribbon 14A the ribbon slips on the drum. The other pipe 42 draws a higher vacuum in internal chamber 85 to assure that the cut off segments 14 hold an exact position on drum 20. A knife roll 24 is provided on shaft 34 in this example. It has eight knives such as the one marked 33. These knife edges rotate into contact with the periphery of vacuum drum 20 and use the drum as an anvil for cutting individual segments 14 from elastic ribbon 14A. The segments are carried rotationally on vacuum drum 20 until they reach a lowermost position where they are picked off of the vacuum drum by segment transfer means 21 which stretches the segments and transfers them to sheet 13 which runs over transfer roll 22 which serves as a backup member for the sheet or web when an elastic ribbon segment is being pressed onto it. Roll 22 is provided with a silicone rubber cylindrical sleeve 35 which inhibits slipping between sheet 13 and the roll 22 and provides resiliency for pressing the segment on the sheet. Sheet 13 could be run over a backup member in the form of a flat platen, not shown, covered with a resilient layer, instead of running it over roll 22 for applying the stretched segments to the web. Shaft 37 of the transfer roll 22 and shaft 38 of presser 23 are journaled for rotation in bearing structures which are mounted in upstanding frame plates 44 and 43 as can be seen in FIG. 4. Frame plates 40 and 41, in which other rotating parts are journaled, are visible in FIGS. 4 and 8.

Referring to FIG. 3 again, a glue or adhesive applicator 45 is shown placed over a backup roll 47 for sheet 13. It has a row of nozzles 46 which extend transversely across nonwoven sheet 13. Glue applicator 45 lays down tiny stripes of glue which may be continuous or intermittent. By way of example, the stripes may be about 1/32 inch wide and are spaced from each other by about ⅛ inch across the width of the facing sheet 13. As will be explained in more detail later, the transfer device 21 picks an unstretched elastic segment 14 off of the bottom of vacuum drum 20 and rotates it around while stretching it and deposits it on sheet 13, before or after the sheet is incorporated in the web, where it makes tangential contact with the silicone rubber sleeve 35 on backup transfer roll 22. The stretched elastic segment 14 then adheres to moving sheet 13. The segment 14 is carried around transfer roll 22, in the illustrated model, about one-half revolution where it is caused to interface with the plastic backing sheet 10 of the diaper web. Some models of the machine provide for pressing the elastic segments 14 onto the nonwoven sheet 13 or on a side of one of the sheets 10 or 13 that leaves the segment exposed rather than between the sheets. FIG. 3 shows absorbent pads 11 being transported on a conveyor belt 48 which runs around a roller 49. The backing sheet 10 is fed in over a roll 50 after which the absorbent pads are applied to the backing sheet. One may see in FIG. 2 that the elastic segment 14 is deposited in the space between two consecutive absorbent pads 11. The backing sheet has also had fine intermittent or continuous glue stripes applied to its top surface at a station, not shown, which precedes roll 50. The stripes cause the absorbent pads to adhere to backing sheet 10 and cause the stretched elastic band 14 to adhere to the backing sheet so the segment is now adhered in stretched condition to backing sheet 10 and to facing sheet 13.

Note in FIG. 3 that the transversely extending rotational axes of the vacuum drum 20, the backup transfer roll 22 and the new segment transferring and stretching device 21 all lie on the same vertical plane in this embodiment but they could be in non-vertical planes as long as they are at the proper distance from each other. It should also be noted that the linear velocities of the grippers 51 and 52 of the transfer device 21 periphery and the transfer roll 22 are equal or nearly equal.

The linear velocity of the vacuum drum 20 periphery can be adjustable and depends in one respect on the distance between elastic segments deposited in the moving web. There is one segment 14 at each diaper severance line in the web. So one elastic segment 14 must be presented by drum 20 to transfer device 21 for every diaper length. It is also desirable to slow down the vacuum drum 20 to avoid inaccuracies that result from the elastic ribbon 14A snapping back after a segment 14 is cut from it. One way to compensate for running the vacuum drum slowly is to increase the number of blades 33 in the knife roll 24 so more segments 14 are cut off of ribbon 14A per unit time in which case the segments 14 move more slowly relative to the grippers of the transfer device 21. There must be a space between the elastic segments 14 on vacuum drum 20 for the elastic segments to arrive on the web between individual diapers. Later, when the individual diapers are severed from the web the cut is made through the middle of the elastic segment so half goes to one diaper and half to the next diaper. Hence, the ribbon 14A is restrained by a sufficient amount through coaction of pinch rolls 29 and driven roller 28 principally, for the vacuum drum to slip under ribbon 14A instead of drawing the ribbon along the drum at the linear velocity of the drum. After a segment 14 is cut off it should not slip on drum 20.

Attention is now invited to FIG. 4 for a more detailed description of one embodiment of the new stretch-while-rotating elastic segment transfer device 21.

The device 21 for transferring unstretched elastic segments 14 from vacuum drum 20 to web composing sheet 13 running on transfer roll 22 comprises two gripper units. A typical unit comprises radially extending members 51 and 52 that terminate in grippers 53 and 54. Grippers 53 and 54 are arranged 180° apart in this embodiment but they could be separated by other equal angles in other designs. There is another gripper unit 55. Since both units are the same, only the unit containing grippers 53 and 54 will be described in detail. Members 51 and 52 are fastened to a shaft 59 so they rotate with the shaft. The members are much like spokes of a wheel. In some cases more than one pair of grippers are used. The shaft is journaled in a bearing structure 60 mounted in machine frame member 41. Shaft 59 is driven rotationally through the agency of a toothed pulley 61 which is driven by a timing belt, not shown, running from a pulley 72 on a common shaft with a pulley 73 which is driven by a timing belt 74 running on a pulley 92 on a jack shaft 62. The bearing structure 60 is mounted in frame 41 in such manner that shaft 59 is at an acute angle relative to a horizontal line that is parallel to the axes of vacuum drum 20 and transfer roller 22. Note in FIG. 4 that a vacuum head 63 is provided with bearings 71 so the shaft 29 can rotate in the stationary vacuum head 63. The vacuum head 63 has passageways such as the one marked 64 which communicate with passageways 65 leading to and through one contact area 67 on gripper 56 for example.

Typical gripper 56 is illustrated in FIG. 6 in more detail. It shows that vacuum passageways 65 terminate in holes, such as the one marked 68, which allow application of a vacuum or drawing force to an unstretched elastic segment such as the one marked 14 on vacuum drum 20 in FIG. 4. FIG. 6 shows further that the gripper end area 67 is provided with a plurality of pins 69 which are like the tips of needles. When gripper area 67 interfaces with the periphery of the vacuum drum 20 the needles engage the ends of the yet unstretched elastic segment 14 and assure, in addition to vacuum gripping, mechanical positive gripping of the elastic segments 14 at their ends while they are being stretched.

FIG. 7 shows an alternative embodiment of a gripper where the area 67 has a surface from which sharp granular pieces or crystals 70 project. This is an alternative to using pointed pins 69. Another alternative would be to serrate or knurl the area 67 to produce pointed facets.

In FIG. 3, the tube that applies vacuum to a typical header 63 of the transfer device is marked 75. The location on vacuum head 63 where the tube connects is also depicted in hidden lines in FIG. 8.

Referring again to FIG. 4, the rotated and angulated gripper units are coupled by means of a universal joint indicated generally by the numeral 76. Typical angulated shaft 59 has a yoke 77 mounted on it and there is a pin 78 through this yoke. A clevis having a cross pin 79 passes through pin 78 to provide for all degrees of freedom of rotation and swiveling. A clevis similar to the one marked 77 is mounted to the end of the angulated shaft 50 of the other gripper unit. The universal joints are interconnected by means of a sliding connection 81, which has an internal spline 282 (FIG. 5) for effecting a driving or follower connection from one rotating gripper unit to the other. The shaft 80 for the follower gripper unit is journaled in a bearing structure 82 which is mounted in machine frame member 40.

FIG. 4 shows gripper 53 on one gripper unit and its counterpart 58 on the other unit in engagement with an unstretched elastic segment 14 which is about to be removed from vacuum drum 20 and transferred to moving sheet 13 which is running on the silicone rubber sleeve 35 of backup or transfer roll 22. At the moment, the multiplicity of pins 69 extending from the flat face of the gripper portion 67 have engaged the unstretched elastic segment 14. An enlargement of what is happening is depicted in FIG. 5. Note that the elastic segment 14, besides being mechanically engaged by means of the pointed pins, is being peeled off of the vacuum drum 20 gradually. Vacuum or suction created in the ports 68 (not visible in FIG. 5, see FIG. 6) in the gripper 51 attracts the elastic segment and assists in holding it as it is being rotated around and stretched and applied to sheet 13 where the stretched segment is marked 14B as in FIG. 4. Note in FIG. 5 that high vacuum internal passageway 85 of the drum 20 is terminated inside of the drum just about in alignment with the midline of the gripper so that vacuum to the ports 31 in the vacuum drum is cut off where the segment 14 is being removed from the vacuum drum.

As will be evident in FIG. 4, when the grippers 53 and 58 on the opposite gripper units are rotated 180°. to the position in which grippers 54 and 56 are presently in, the grippers on each of the gripper units have spread axially away from each other to stretch the elastic segment 14 by the desired amount by the time it is applied to the sheet 13 running over backup roll 22.

One may see in FIGS. 6 and 4, for example, that the grippers have an area 83 which is at an acute angle relative to surface area 67 on the grippers. When, as in FIG. 4, a pin containing area 67 is engaging elastic segment 14, area 83 is at an acute angle relative to the surface of vacuum drum 20. As the gripper units rotate around 180° as in FIG. 4 to press the elastic segment toward the transfer roll 22, flat area 83 of the gripper is parallel to and lying on the sheet 13 so as to squeeze the elastic segment 14 onto the adhesive stripe containing sheet 13.

Figure 8:
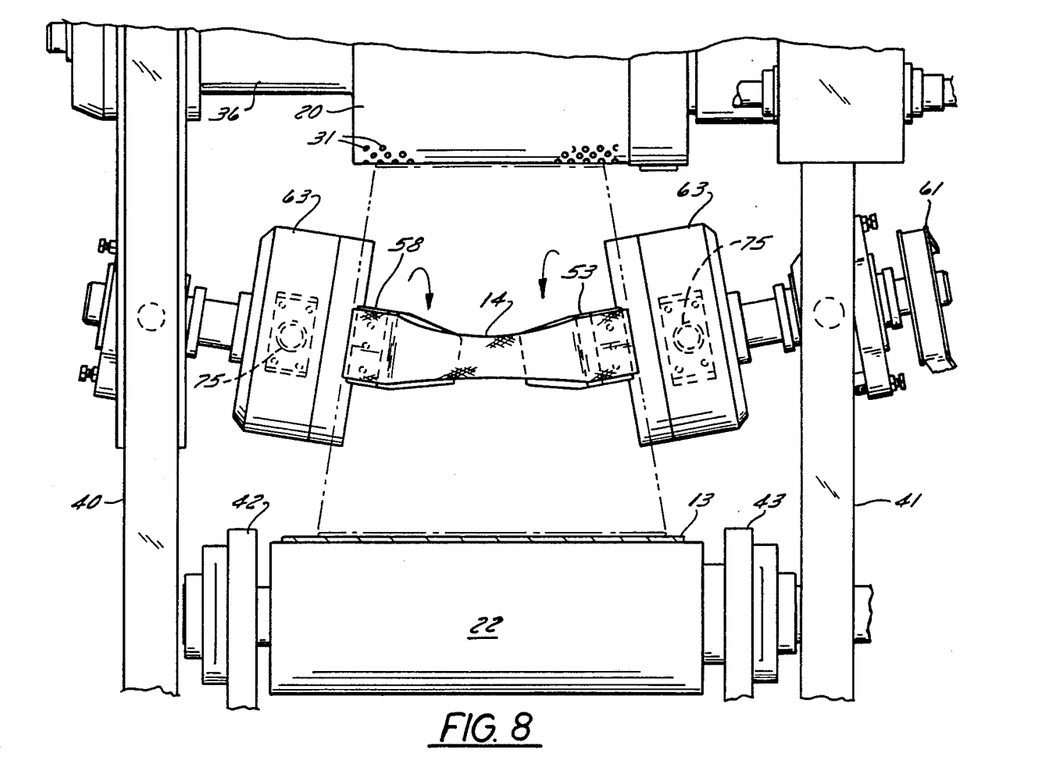
FIG. 8 is a front elevational view showing an elastic band undergoing stretching and rotation after it has been removed from a vacuum drum and is on its way to be deposited on a glue treated sheet that is running over a transfer roll.

FIG. 8 shows an elastic element 14 in about a 50% stretched condition at a time when it is about one-half of the way through its orbit from vacuum drum 20 to transfer roll 22.

After the stretched segment 14B is pressed onto sheet 13 as in FIG. 4, the segment is carried around the sheet backup member, in the form of roll 23, by sheet 13 to the bottom of the roll as shown in FIG. 3. At this time, presser element 23 rotates around to the position in which it is shown for squeezing the entire length of the elastic segment between the adhesive treated interfacing surfaces of the porous or nonwoven sheet 13 and the plastic backing sheet 10 of the diaper web.

In FIG. 4 there are several pulleys such as those marked 91-94 on jack shaft 62. Pulley 93 has a power input belt 95 driving it. All of the belts and pulleys are of the type that are used for timing or keeping rotating machine parts in proper phase relationship. As indicated earlier rolls 25 and 26 are connected by gears, not visible, in box 97 which are driven by a dc motor, not shown. The shafts for these rolls are marked 25S and 26S, respectively, in FIG. 4. Pulley 94 drives knife roll 24 (FIG. 3) which, in turn, drives the vacuum drum 20 by way of gears, not visible, and drives roll 28 (FIG. 3) by way of a timing belt. Pulley 92 drives transfer means 21 (FIG. 3). Pulley 91 drives pulley 90 on the shaft 38 of presser 23. Transfer roll 22 (FIG. 3) is driven synchronously with a timing belt, not shown, downstream in the diaper fabricating machine. The peripheral speed of roll 22 is equal or nearly equal to that of transfer means 21.

Vacuum drum 20 is fastened to a rotatably driven shaft 101. An annular chamber 102, as shown in FIG. 4, is held against rotation but makes a sliding connection to shaft 101 and the drum 20. Chamber 102 contains the passageways 84 and 85 for communicating vacuum to holes 31 in the drum periphery. Pipe 32 (FIG. 5) connects to chamber 84 and to a low vacuum source, not shown. Pipe 42 connects to chamber 85 and to a higher vacuum source, not shown.

Figure 9:
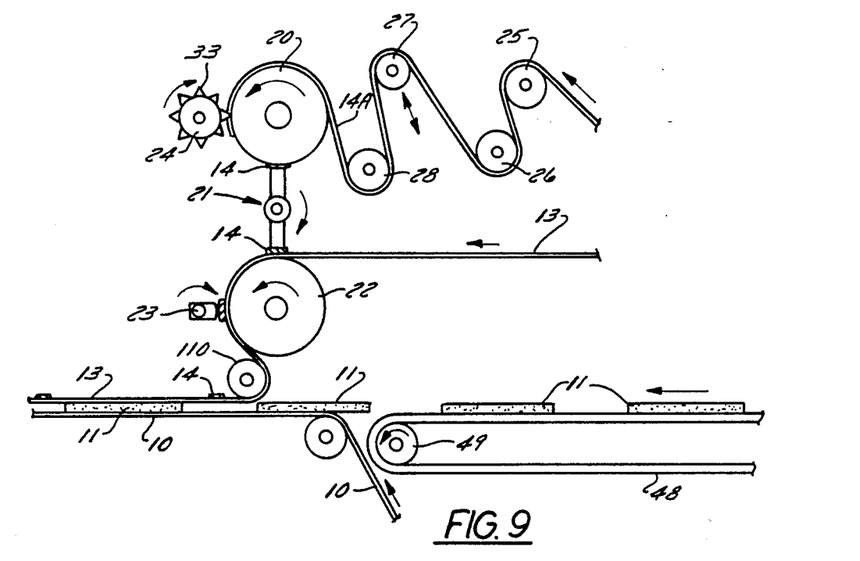
FIG. 9 is a diagram showing how the elastic segment stretching-while-rotating transfer device can be used to apply elastic waistband segments to a diaper to have the band itself interface with the body.

FIG. 9 is a diagram of an arrangement for using the new stretch-while-rotating transfer device 21 for applying elastic waistband segments 14 to the side of the nonwoven sheet 13 of the diaper which would interface with the wearer's body instead of having the elastic segment between the nonwoven sheet 13 and the moisture impermeable backing sheet 10 as in the previously discussed embodiment. Parts in FIG. 9 which are the same as in the previously described embodiment are given the same reference numerals.

In FIG. 9 elastic ribbon 14A is fed to vacuum drum 20 after having passed over interengaged rolls 25 and 26, dancer roll 27 and roll 28. Knife roll 24 cuts the elastic segments 14 from the ribbon, using the drum as an anvil as before. Stretch-while-rotating transfer device 21 functions as before where it accepts an elastic segment 14 from the vacuum drum and presses it into fluid permeable nonwoven sheet 13. In this case, however, there are no continuous fine glue lines on sheet 13. Instead, glue is applied intermittently to sheet 13 over longitudinally spaced areas that are about equal to the area of an elastic segment. In FIG. 9, the elastic segment 14 that is just being applied by transfer device 21 to sheet 13 where it is tangent to transfer roll 22, covers the glue area on the sheet 13. Hence, as sheet 13 passes presser 23 and passes over roll 110 all glue is covered. It should be evident, however, it could be the plastic backing sheet 10 that is run over backup or transfer roll 22 instead of nonwoven sheet 13 in which case the elastic segments 14 would be applied to the plastic backing sheet 10 instead of sheet 13. Impermeable backing sheet 10 has continuous glue stripes applied to provide for bonding absorbent pads 11 to the backing sheet and for adhering the margins, at least, of the nonwoven 13 and impermeable sheet 10 together.

Figure 10:
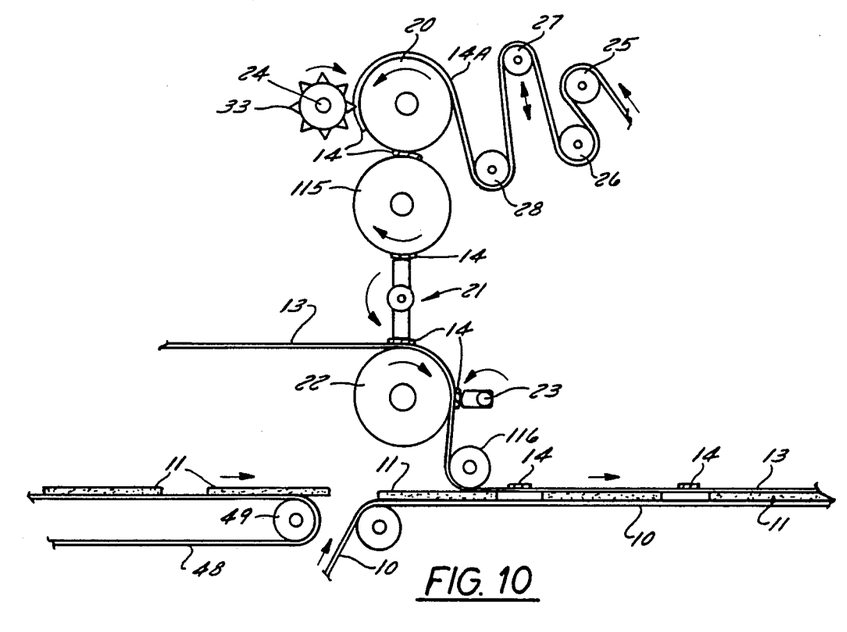
FIG. 10 is a diagram showing how the new transfer device can be used to apply elastic segments to the waistband region when the segments are driven from a ribbon of elastic material that has pressure sensitive adhesive on one side over its entire length.

FIG. 10 is a diagram of another arrangement in which the new elastic segment transfer device 21 is utilized. This arrangement provides for utilizing an elastic ribbon 14A that is coated entirely on one side with pressure sensitive adhesive. In this case, as before, ribbon 14A has segments 14 severed from it by knife roll 24. When the ribbon 14A runs onto vacuum drum 20 the pressure sensitive adhesive or sticky side of the ribbon is facing out and away from vacuum drum 20. Infeed rolls 26 and 28 are preferably coated with a release agent such as silicone or a material known by the trademark Teflon which are commonly used for this purpose.

The FIG. 10 arrangement differs from the others for reason of including an additional vacuum drum 115 intermediate of cut off vacuum drum 20 and transfer device 21. The linear speed of intermediate drum 115 is about the same as the speed of the diaper web. Drum 115 is coated with a release agent. The sticky side of an elastic segment 14 interfaces with drum 15 but the release agent provides for easy pick off of segment 14 from intermediate vacuum drum 115. After pick off, as before, the elastic segments 14 are applied to nonwoven fluid permeable sheet 13 where it becomes tangent to transfer roll 23. After elastic segments 14 are pressed on, sheet 13 goes around a roller 116 to be joined with backing sheet 10 which has fine glue lines on it and has had the absorbent pads applied after they have been delivered by conveyor 48.

Figure 11:
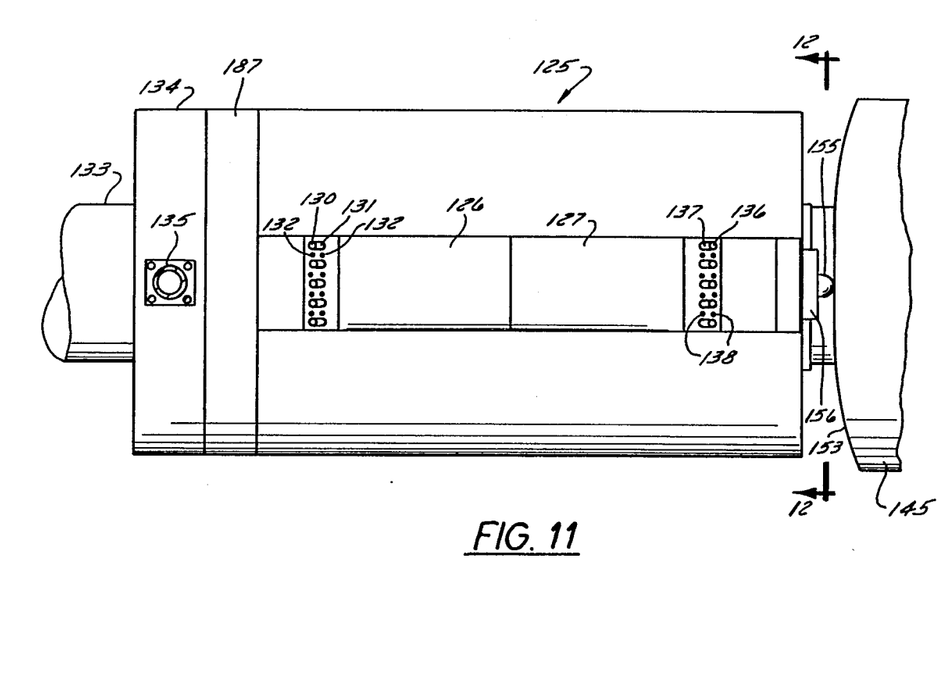
FIG. 11 is a plan view of another embodiment of the segment transferring device.
Figure 12:
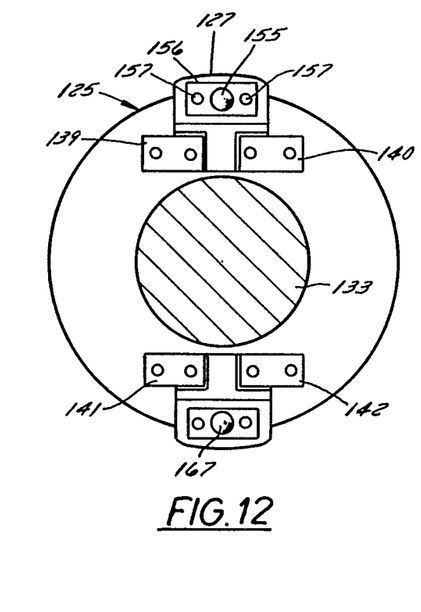
FIG. 12 is a section corresponding to the line 12—12 in FIG. 11.
Figure 13:
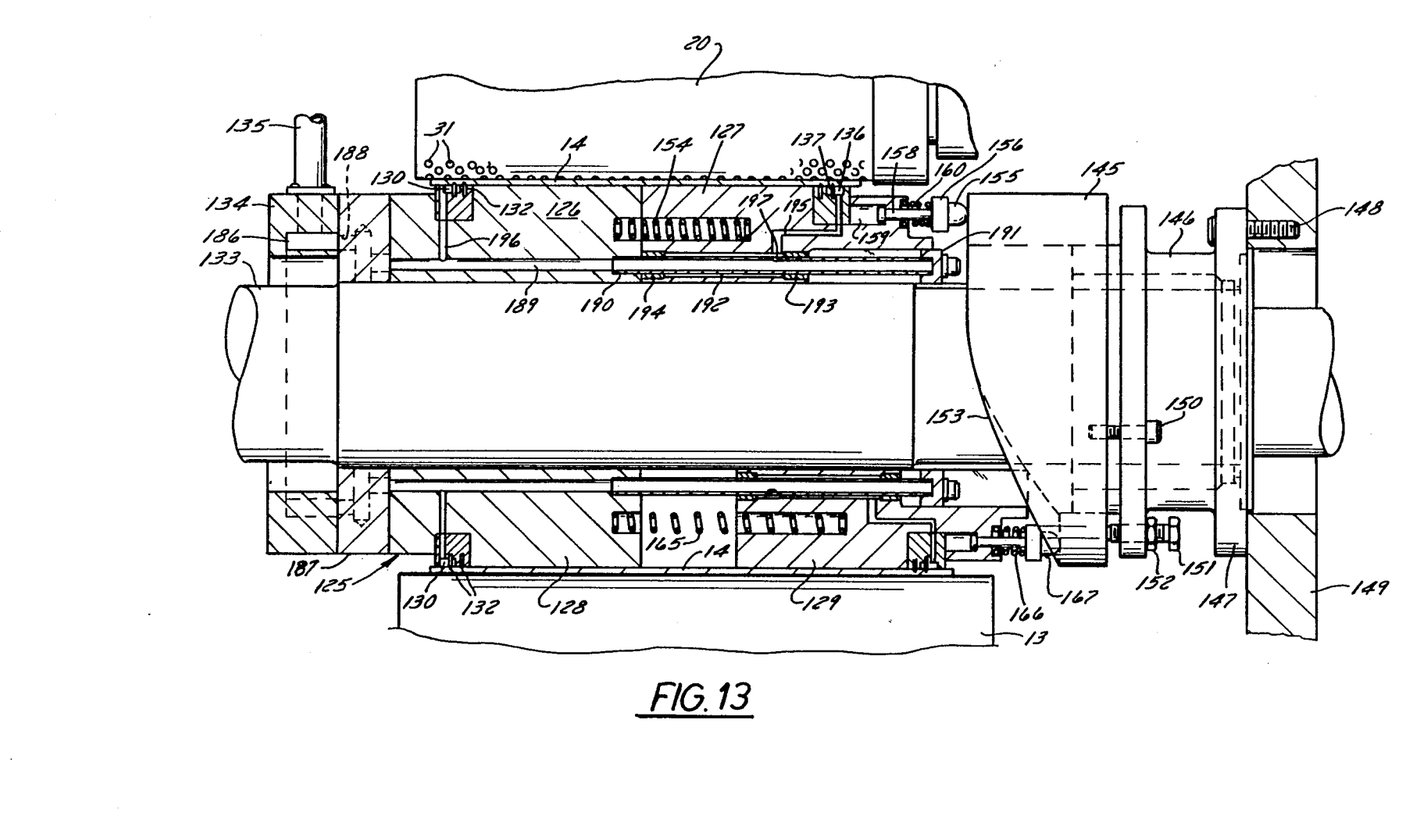
FIG. 13 is a side elevational view of the device in FIG. 11, partly in vertical section.

FIGS. 11–13 show another implementation of the stretch-while-rotating concept. The elastic segment stretching and transferring device 21 is shown isolated from the diaper fabricating machine but it will be understood that it will be positioned between vacuum drum 20 and sheet 13 which overlays backup roll 22 as in the previously described embodiment. FIG. 13 shows a part of vacuum drum 20 and a top view of moving sheet 13.

Referring to FIG. 11, the transfer device comprises a rotor generally designated by the numeral 125. A pair of grippers 126 and 127 are mounted in rotor 125. Gripper 126 is fixed in the rotor. Gripper 127 is slidable axially.

As shown in FIGS. 11 and 13, movable gripper 127 is presently as close as it can get to fixed gripper 126. In this particular embodiment, as can be seen in FIG. 13, there is another pair of grippers 128 and 129 diametrically opposite on the rotor from grippers 126 and 127. Gripper 128 is fixed in the rotor and gripper 129 is reciprocable axially relative to fixed gripper 128. In some cases, more than two pairs of grippers are mounted in the rotor. As shown in the FIG. 11 plan view, stationary gripper 126 has a plurality of vacuum ports 130. There are slots such as the one marked 131 for increasing the area over which the vacuum can be applied to the elastic segment 14. The grippers have a plurality of rather sharp elements such as pins 132 adjacent the vacuum ports, similar to the sharp pins 69 which were used in the previously described embodiment to supplement the gripping force on the elastic segment which force is created by the vacuum ports. Rotor 125 is fastened to a shaft 133 for rotating with it. A vacuum header 134 is secured against rotation and there is a vacuum pipe or hose 135 connected to the header. Typical axially reciprocable gripper 127 also has a plurality of vacuum ports 136 which terminate in the bottom of slots 137. Gripping supplementing pins 138 are also projecting from gripper 127 to supplement the vacuum attractive force on the elastic segment 14.

FIG. 12 shows how the axially reciprocable grippers 127 are slidable in ways such as those marked 139-142 which are fixed in rotor 125.

The internal structure of the transfer device can be seen best in FIG. 13 to which attention is now invited. The grippers 127 and 129 are reciprocated by using a stationary cam 145. The cam is mounted on an adapter 146 which has a flange 147. One of the several machine bolts 148 is shown, which fasten the flange and consequently the cam to a part 149 of the machine frame. The cam 145 is secured on the adapter by means of a plurality of machine bolts such as the one that is depicted and is marked 150. There are also a plurality of bolts such as the one marked 151 which are used to position the cam accurately. Each bolt 151 is provided with a lock nut 152 for maintaining the adjusted position of the cam. The cam is formed from a hollow cylinder which is shaped to provide the appropriate cam profile 153. A preloaded compression spring 154 is interposed between stationary gripper 126 and axially reciprocable or movable gripper 127. Spring 154 tends to force axially movable gripper 127 away from fixed gripper 126. Grippers 126 and 127 are presently near to each other since they are being pressed together by the force of a rounded cam follower head 155 which is presently bearing on the axially longest part of the cam contour or profile. The cam follower includes a cross member 156 which guides the follower by sliding on a pair of guide pins 157 which are visible in FIG. 12. In FIG. 13, one may see that the cam follower includes a headed stem 158 which is movable in a bore 159. A spring 160 is interposed between the cam follower and the rotor. One purpose of this spring is to maintain the cam follower element 155 in good contact with the contour of the cam as the gripper assembly rotate contiguous to the cam. Cam follower spring 160 transmits the force from the follower element 155 to movable gripper 127 which brings gripper 127 nearer to fixed gripper 126.

As one may see in FIG. 13, when the grippers are rotated to the position in which grippers 128 and 129 presently reside, the compression spring 165, which is interposed between grippers 128 and 129, has forced movable gripper 129 farther from fixed gripper 128. At this time, follower compression spring 166 assures that follower head 167 is pressed against the cam profile 153. The cam follower structure associated with gripper 129 is, of course, the same as the one associated slidable gripper 127 so the former need not be discussed in greater detail.

The manner in which vacuum is applied to the groups of ports 130 and 137 will now be described in reference to FIG. 13. The vacuum systems for grippers 126 and 127 is identical to the system for grippers 128 and 129 so only the former will be described. The vacuum header 134 has an annular passageway 186. An annular member 187 which is rotatable with the rotor has an annular channel 188 to which the vacuum from conduit 135 is applied. The vacuum effect is propagated to an axial hole 189 in fixed gripper 126. There is a tube 190 whose end is fixed in gripper 126. The other end of tube 190 has a cap 191 for closing the end of the tube. In movable gripper 127 there is a bore 192 that provides a space concentrically around tube 190. There are seals 193 and 194 in gripper 127 which close the ends of bore 192 and provide for the gripper and its bore 192 to slide along the outside of tube 190 whose inside is under vacuum. Tube 190 has a hole 197 in its wall for communicating vacuum to a generally s-shaped duct 195 which terminates in the group of vacuum ports 137. Thus, it will be seen that gripper 127 can slide along tube 190 and maintain vacuum on ports 137. The group of ports 131 in stationary gripper are supplied directly from bore 189 through a duct 196.

Operation of the FIGS. 11-13 implementation of the new transfer device will now be briefly described. In FIG. 13, the rotor is at a rotational position wherein stationary gripper 126 and its cooperating movable gripper 127 are both engaged with an unstretched elastic segment and are about to strip the segment 14 from vacuum drum 20 due to rotation of the rotor. As the rotor continues to rotate, the cam follower 155 follows the axially receding cam profile 153 which allows compression spring 154 to separate gripper 127 from gripper 126 in which case the elastic segment 14 undergoes stretching. When the grippers arrive in the position in which grippers 128 and 129 are presently shown, elastic segment 14 is stretched to its desired limit and is overlaying sheet 13 to which it is applied by grippers 128 and 129. In this case, sheet 13 has had continuous longitudinally extending glue stripes, not visible, applied to its surface so that stretched segment 14 is gripped by the glue. Thus, the stretched segment transfers to the sheet 13.

The annular passageway 186 in vacuum head 134 at the left end of the rotor assembly in FIG. 13 can be rotated so the vacuum cut off point can be adjusted precisely to yield the stretched segment to the moving sheet 13.

In FIGS. 3, 9 and 10, for example, the elastic segments 14 are adhered directly to nonwoven sheet 13 as it runs over a backup member in the form of silicone rubber coated roller 22. Running plastic backing sheet 10 over backup member 22 and applying the segments to the plastic sheet 10 before it is joined with sheet 13 and absorbent pads 11 to form a continuous web of diapers has been mentioned. Further, it should be understood that the elastic segments 14 can be applied to the assembled diaper web, depicted in FIG. 2, composed of sheets 10 and 13 and absorbent pads 11, such as the web running off to the left in FIG. 9. All that would be necessary would be to assemble the web before it runs over a backup member such as roll 22 and then apply the elastic segment 14 as the web passes over the roll.

Although embodiments of the new apparatus for stretching an elastic segment while rotating it and then applying it to a moving web have been described in detail, such description is intended to be illustrative rather than limiting, for the invention may be variously embodied and is to be limited only by interpretation of the claims which follow.

We claim:

1. Apparatus for applying stretched elastic segments to the waist regions of a moving web of diapers or other body wearable garments of at least two interfacing sheets and absorbent pads arranged equally spaced apart between said sheets, said apparatus including:

a rotatable vacuum drum, means for disposing unstretched segments of elastic material consecutively on the periphery of said drum, said segments being attracted to said drum by vacuum and rotatable with the drum, a backup member over which at least one of said sheets comprising said web is run, transfer means interposed between said vacuum drum and said member for transferring said segments directly from said drum to said sheet, said transfer means comprising at least two segment grippers each having surfaces containing vacuum ports and means for mounting said grippers for simultaneously rotating in angular correspondence between said drum and said surface, means for moving at least one of the grippers alternately nearer to and farther from the other as said grippers rotate, said grippers being nearer to each other when they are in proximity with said drum for attracting under the influence of vacuum an unstretched segment, and said grippers then becoming farther from each other to stretch the segment as the grippers rotate into proximity with said segment backup member for applying said segment to the sheet, and the said surface of the gripper having said vacuum ports being presented generally radially outwardly of said gripper and there is another surface contiguous to said surface and at an acute angle to said surface, said surface being generally parallel to the vacuum drum when said grippers are proximate to the drum and said other surface being at an angle at the same time, said other surface becoming substantially parallel to said backup member when said grippers are proximate to said backup member to provide for pressing said segment onto the sheet running over said member.

2. Apparatus for applying stretched elastic segments to the waist regions of a web of diapers or other body wearable garments comprised of at least two interfacing sheets and absorbent pads arranged equally spaced apart between said sheets, said apparatus including:

a rotatable vacuum drum having a peripheral surface, means for disposing unstretched segments of elastic material consecutively on said surface, said segments being attracted to said drum by vacuum and rotatable with the drum, a backup member over which at least one of said sheets comprising said web is run, said member being spaced from said vacuum drum, transfer means interposed between said vacuum drum and member for transferring said elastic segments consecutively from said drum to said sheet running over said member, said transfer means comprising at least two adjacent units each having rotatably driven radially outwardly extending angularly spaced apart elastic segment grippers and shafts to which said grippers, respectively, are mounted, and means for rotating together said individual shafts whose axes are angulated at respectively opposite acute angles relative to said drum and backup member, corresponding grippers on each unit being separated from each other in an axial direction by a predetermined amount when said grippers are rotated proximate to said vacuum drum for gripping an unstretched elastic segment and said grippers separating from each other by a greater amount to stretch said segment when said grippers are rotated proximate to said backup member for applying said segment in stretched condition to said sheet, said grippers having radially outwardly presented areas containing vacuum ports for holding segments attracted from said vacuum drum, said grippers having surfaces extending at an angle relative to said areas and adjacent said areas, said surfaces, being angulated away from said vacuum drum when said areas are proximate to said drum and said surfaces angulating into parallelism with said backup member when said grippers are rotated into proximity with said member for said surfaces to press said segments in stretched condition onto said first sheet as it passes over said member.

* * * * *